(12) United States Patent
Gryczynski et al.

(10) Patent No.: US 9,388,450 B2
(45) Date of Patent: Jul. 12, 2016

(54) FRET BASED MULTIPLEX PROBES

(71) Applicants: University of North Texas Health Science Center at Fort Worth, Fort Worth, TX (US); Texas Christian University, Fort Worth, TX (US)

(72) Inventors: Zygmunt Gryczynski, Fort Worth, TX (US); Ignacy Gryczynski, Fort Worth, TX (US); Rafal Fudala, Fort Worth, TX (US); Badri P. Maliwal, Fort Worth, TX (US)

(73) Assignees: UNIVERSITY OF NORTH TEXAS HEALTH SCIENCE CENTER, Fort Worth, TX (US); TEXAS CHRISTIAN UNIVERSITY, Fort Worth, TX (US)

( * ) Notice: Subject to any disclaimer, the term of this patent is extended or adjusted under 35 U.S.C. 154(b) by 133 days.

(21) Appl. No.: 14/206,738

(22) Filed: Mar. 12, 2014

(65) Prior Publication Data

US 2014/0274797 A1    Sep. 18, 2014

Related U.S. Application Data

(60) Provisional application No. 61/777,727, filed on Mar. 12, 2013.

(51) Int. Cl.
  *C12Q 1/37* (2006.01)
  *C07H 21/04* (2006.01)

(52) U.S. Cl.
  CPC .................................... *C12Q 1/37* (2013.01)

(58) Field of Classification Search
  None
  See application file for complete search history.

(56) References Cited

U.S. PATENT DOCUMENTS 6,743,325 B1    6/2004 Taylor
8,609,329 B2    12/2013 Barroso et al.

*Primary Examiner* — James Martinell
(74) *Attorney, Agent, or Firm* — Chainey P. Singleton; Edwin S. Flores; Chalker Flores, LLP (57) ABSTRACT

The present invention includes compositions and methods for fluorescence-based multiplex probe to simultaneously detect one or more enzymatic activities comprising: a first enzymatic target having a first end and a second end, wherein the first end of the first enzymatic target is attached to a central body and the second end of the first enzymatic target is attached to a first fluorophore; a second enzymatic target having a first end and a second end, wherein the first end of the second enzymatic target is attached to the central body and the second end of the second enzymatic target is attached to a third fluorophore; wherein the central body comprises at least one second fluorophore; wherein the first enzymatic target comprises a specific cleavage site of a first enzyme that cleaves the first enzymatic target; and wherein the second enzymatic target comprises a specific cleavage site of a second enzyme.

18 Claims, 7 Drawing Sheets

FRET BASED MULTIPLEX PROBES

CROSS-REFERENCE TO RELATED APPLICATIONS

This application claims priority based on U.S. Provisional Application No. 61/777,727, filed Mar. 12, 2013. The contents of which is incorporated by reference in its entirety.

STATEMENT OF FEDERALLY FUNDED RESEARCH

This invention was made with U.S. Government support under Contract No. R01 EB01200 awarded by the NIH. The government has certain rights in this invention.

TECHNICAL FIELD OF THE INVENTION

The present invention relates in general to the field of probes, and more particularly, to FRET based multiplex probes.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Mar. 10, 2014, is named UNTF1032_SL_ST25_031214.txt and is 2,048 bytes in size.

BACKGROUND OF THE INVENTION

Without limiting the scope of the invention, its background is described in connection with multiplex probes.

Current methods of protease activity detection involve fluorescence detection using selectively activated probes. Enzyme-linked immunoassay (ELISA) based methods for the detection of this enzyme take advantage of the sensitivity of fluorescence measurements. All of these techniques, however, involve multiple, time-consuming steps. The length of the process combined with the expense and the expertise involved in the setup/analysis of these techniques make them impractical for clinical practice.

One such system is taught in U.S. Pat. No. 8,609,329, issued to Barroso, et al., which is directed to a FRET-based assay for screening modulators of receptor cycling. Briefly, these inventors teach an automated FRET imaging of membrane-bound receptor/ligand complexes that is said to discriminate between a clustered organization of ligand/receptor complexes that occurs during the early endocytic stages following internalization and a random distribution characteristic of late stage disassociation of ligand from the receptor.

Another system is taught in U.S. Reissue Pat. No. RE42,325, to Wittwer, et al., which is directed to a homogeneous multiplex hybridization analysis by color and Tm. Briefly, this invention is said to provide methods and devices for analyzing sequence variations in nucleic acid samples that include multiple loci, each having two, three or more possible allelic sequences. The method is said to involve combining at least a first and second pair of oligonucleotide probes with the nucleic acid sample. The first pair of probes is capable of hybridizing in proximity to each other within a segment of the nucleic acid sample comprising the first locus and the second pair is capable of hybridizing in proximity to each other within a segment of the nucleic acid sample comprising the second locus. The first member of each probe pair comprises a FRET donor and the second member comprises a FRET acceptor, the FRET acceptor of the first probe pair member having a different emission spectrum from the FRET acceptor of the second probe pair. Upon hybridization, the proximity of the first and second member of each probe pair is sufficient to allow fluorescence resonance energy transfer between the FRET donor and the FRET acceptor.

SUMMARY OF THE INVENTION

In one embodiment the present invention includes a fluorescence-based multiplex probe to simultaneously detect one or more enzymatic activities comprising: a first enzymatic target having a first end and a second end, wherein the first end of the first enzymatic target is attached to a central body and the second end of the first enzymatic target is attached to a first fluorophore; a second enzymatic target having a first end and a second end, wherein the first end of the second enzymatic target is attached to the central body and the second end of the second enzymatic target is attached to a third fluorophore; wherein the central body comprises at least one second fluorophore; wherein the first enzymatic target comprises a specific cleavage site of a first enzyme that cleaves the first enzymatic target; and wherein the second enzymatic target comprises a specific cleavage site of a second enzyme. In one aspect, the first fluorophore has a shorter wavelength of absorption then the second fluorophore, and the second fluorophore has a shorter wavelength of absorption then the third fluorophore. In another aspect, the fluorescent emission peak of the first fluorophore overlaps with an excitation peak of the second fluorophore, and wherein a fluorescent emission peak of the second fluorophore overlaps with an excitation peak of the third fluorophore. In another aspect, the first fluorophore is defined as donor chromophore for the second fluorophore; wherein the second fluorophore is defined as acceptor chromophore of the first fluorophore and further defined as donor chromophore for the third fluorophore; and wherein the third fluorophore is defined as acceptor chromophore for the second fluorophore. In another aspect, the first fluorophore comprises FITC, the second fluorophore comprises TAMRA, and the third fluorophore comprises Cy5. In another aspect, the energy transfer from first fluorophore is forced to the second fluorophore by, for example, close proximity. In another aspect, the energy transfer from first fluorophore is forced to the second fluorophore through enhanced interaction with multiple second fluorophores positioned on the central body. In another aspect, the direct energy transfer from the first fluorophore to the third fluorophore is limited by for example spatial separation forced by the central body. In another aspect, the first or second enzyme is a matrix metalloproteinase. In another aspect, the first or second enzyme is an endopeptidase. In another aspect, the first or second enzyme is a nuclease, a restriction enzyme, a proteinase, a lipidase, or a saccharidase. In another aspect, the enzymatic target is a peptide, a nucleic acid, a lipid or a polysaccharide.

Another embodiment of the present invention includes a fluorescence-based multiplex probe to simultaneously detect two or more proteinase activities comprising: at least one first oligopeptide having a first end of the first oligopeptide and a second end of the first oligopeptide, wherein the first end of the first oligopeptide is attached to a central body and the second end of the first oligopeptide is attached to a first fluorophore; at least one second oligopeptide having a first end of the second oligopeptide and a second end of the second oligopeptide, wherein the first end of the second oligopeptide is attached to the central body and the second end of the second oligopeptide is attached to a third fluorophore;

wherein the central body comprises at least one second fluorophore; wherein the first oligopeptide comprises a specific cleavage site of a first proteinase; and wherein the second oligopeptide comprises a specific cleavage site of a second proteinase. In one aspect, the first fluorophore has a shorter wavelength absorption then the second fluorophore, and the second fluorophore has a shorter wavelength absorption then the third fluorophore. In another aspect, the fluorescent emission peak of the first fluorophore overlaps with an excitation peak of the second fluorophore, and wherein a fluorescent emission peak of the second fluorophore overlaps with an excitation peak of the third fluorophore. In another aspect, the first fluorophore is defined as donor chromophore for the second fluorophore; wherein the second fluorophore is defined as acceptor chromophore of the first fluorophore and further defined as donor chromophore for the third fluorophore; and wherein the third fluorophore is defined as acceptor chromophore for the second fluorophore. In another aspect, the first fluorophore comprises FITC, the second fluorophore comprises TAMRA, and the third fluorophore comprises Cy5. In another aspect, the direct energy transfer from the first fluorophore to the second fluorophore is disabled by an enzyme. In another aspect, the first or second proteinase is a matrix metalloproteinase (MMP). In another aspect, the first or second proteinase is an endopeptidase. In another aspect, the central body is a nanoparticle. In another aspect, the central body comprises a spacer that limits direct contact of the first and the second oligopeptide. In another aspect, the central body comprises a protein. In another aspect, the central body comprises avidin. In another aspect, the first or the second oligopeptide comprises a specific cleavage site for metalloproteinase-9 (MMP-9). In another aspect, the first or the second oligopeptide comprises a specific cleavage site for metalloproteinase-2 (MMP-2). In another aspect, the first or the second oligopeptide comprises at least one specific cleavage site selected from the group consisting of optimal peptide substrates for a consensus for MMP-2 (Lys-Gly-Ser-Gly-Pro-Tyr-↓*-Val-Ile-Trp-Leu-Gly-Lys) (SEQ ID NO.: 6). In another aspect, the first or the second oligopeptide comprises at least one sequence selected from the group consisting of optimal substrate (peptide sequence) consensus for MMP-9 (Lys-Gly-Pro-Arg-Ser/Thr-↓*-Leu/Ile-Ser/Thr-Gly-Lys) (SEQ ID NO.: 7).

Yet another embodiment of the present invention includes a method of simultaneously detecting proteinase activity of at least two proteinases in a sample comprising: obtaining the sample; obtaining a fluorescence-based multiplex probe, the probe comprising at least one first oligopeptide having a first end of the first oligopeptide and a second end of the first oligopeptide, wherein the first end of the first oligopeptide is attached to a central body and the second end of the first oligopeptide is attached to a first fluorophore; at least one second oligopeptide having a first end of the second oligopeptide and a second end of the second oligopeptide, wherein the first end of the second oligopeptide is attached to the central body and the second end of the second oligopeptide is attached to a second fluorophore; wherein the central body comprises at least one third fluorophore; wherein the first oligopeptide comprises a specific cleavage site of a first proteinase, wherein the second oligopeptide comprises a specific cleavage site of a second proteinase; combining the sample with the fluorescence-based multiplex probe; exposing the sample to a first excitation wavelength for the first fluorophore and detecting a first emission; exposing the sample to a second excitation wavelength for the second fluorophore and detecting a second emission; relating the first emission to the second emission; second emission to the third; and determining proteinase activity.

Yet another embodiment of the present invention includes a method of diagnosing a patient suspected of being afflicted with a disease comprising: obtaining a sample of the patient; obtaining a fluorescence-based multiplex probe, the probe comprising at least one first oligopeptide having a first end of the first oligopeptide and a second end of the first oligopeptide, wherein the first end of the first oligopeptide is attached to a central body and the second end of the first oligopeptide is attached to a first fluorophore; at least one second oligopeptide having a first end of the second oligopeptide and a second end of the second oligopeptide, wherein the first end of the second oligopeptide is attached to the central body and the second end of the second oligopeptide is attached to a second fluorophore; wherein the central body comprises at least one third fluorophore; wherein the first oligopeptide comprises a specific cleavage site of a first proteinase, wherein the second oligopeptide comprises a specific cleavage site of a second proteinase; combining the sample with the fluorescence-based multiplex probe; exposing the sample to a first excitation wavelength for the first fluorophore and detecting a first emission; exposing the sample to a second excitation wavelength for the third fluorophore and detecting a second emission; relating the first emission to the second emission; determining proteinase activity; and diagnosing cancer upon relating proteinase activity to diagnosis of the disease. In one aspect, the sample is a tumor sample or a tumor sample from a body fluid. In another aspect, the step of diagnosing comprises predicting a therapeutic outcome of an anti-cancer treatment or changing the treatment depending on the presence or absence of markers determined to determine the pharmacokinetics of a treatment for the disease. In another aspect, the disease is cancer.

BRIEF DESCRIPTION OF THE DRAWINGS

For a more complete understanding of the features and advantages of the present invention, reference is now made to the detailed description of the invention along with the accompanying figures and in which:

FIGS. 3A-D. Concept for multiplex probe detection is shown schematically. Two excitation wavelengths in interleave mode can be used (for example 480 nm left and 532 right; the selection of excitation is not limited to these two and can be anywhere within UV/VIS/NIR range). The figure presents expected results for: FIG. 3D—both peptides cleaved. Third long wavelength excitation (in our case 630/650 nm) can be used for control. The long wavelength excitation will give information on the presence of second acceptor.

4 and 5) has been labeled with donor on one end and acceptor on another end. When intact significant (>90%) FRET occurs. Addition of MMP-9 cleaves the peptide separating donor and acceptor. Photography shows the color change induced by cleavage.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes compositions and methods for making and using the new probes that are constructed from a central body of the probe that promotes enhanced (and in some cases exclusive) energy transfer from donor one (first dye) to acceptor one (second dye). This energy transfer process is highly enhanced to compete with transfer from donor one to acceptor two (third dye) allowing for separate monitoring (and therefore the detectable distinction) between cleavage of individual sides. At the same time the central body acts as a physical spacer between donor one and acceptor two.

The American Cancer Society has estimated that about 138,280 new cases of urinary cancer including kidney (64,770) and bladder (73,510) cancer will be diagnosed in the United States in 2012 alone. About 28,450 deaths from kidney (13,570) and bladder (14,880) cancer are expected to occur in this year. Compared to 2010, we can expect 12,530 additional diagnoses of kidney cancer in 2012 (http://www.cancer.org). In renal cell carcinoma (RCC) as well as in bladder cancer (BC), metaloproteinase-2 (MMP-2), metalloproteinase-9 (MMP-9) enzymes overexpression were found. For example, the elevation of MMPs have been shown to be correlated with aggressiveness, grade, survival, and even with early symptoms in localized tumors. Elevated MMP levels in RCC specimens have been also associated with elevated angiogenic factors, suggesting a role for MMPs in tumor invasion.

Alternative combinations of fluorophores for use with the present invention include but are not limited to: a first fluorophore comprises Alexa Fluor 488, a second fluorophore comprises Alexa Fluor 532, and a third fluorophore comprises Alexa Fluor 647. Other alternative include any two dyes system with the quantum dote as a central body (e.g. FITC, 550 QD, Cy5). In certain embodiments a two dye system with the quantum dot (QD) as a central body (e.g., FITC, 550 QD, Cy5). QD can fulfill the role of a second dye (acceptor for the first dye and donor for the third dye).

Figure 2A:
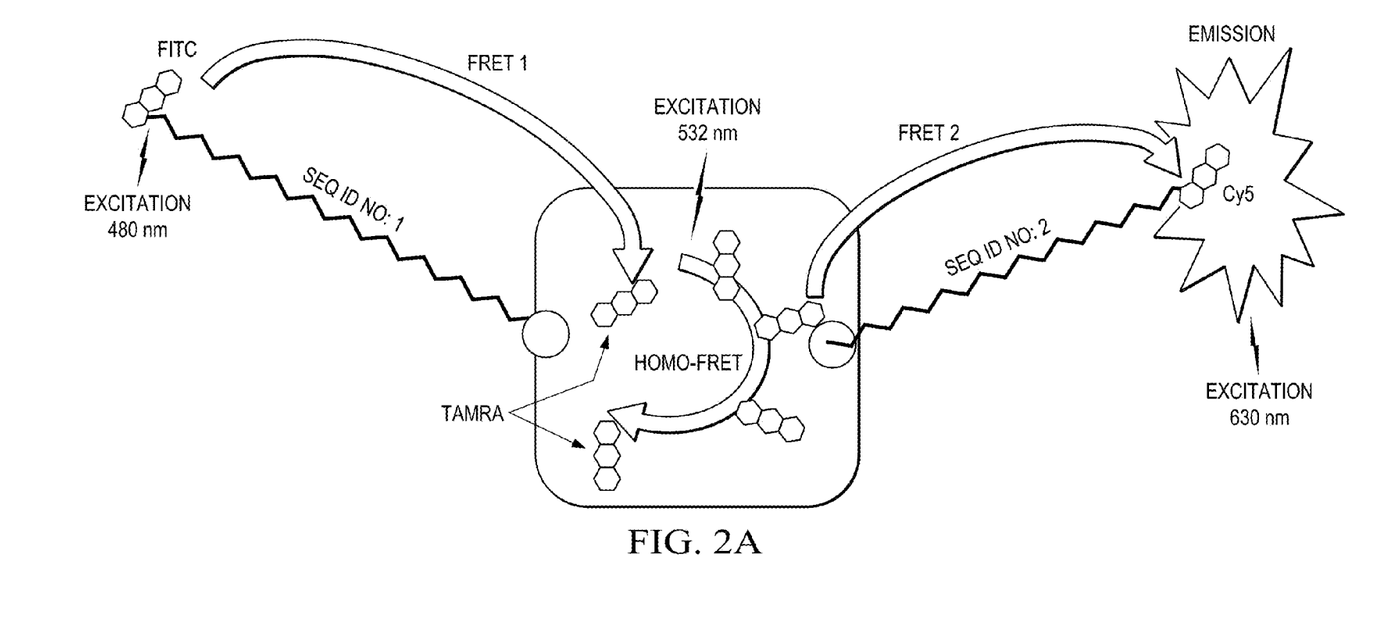
FIG. 2A is another embodiment of the multiplex probe based on the two-step FRET process (SEQ ID NOS.: 1 and 2)
Figure 2B:
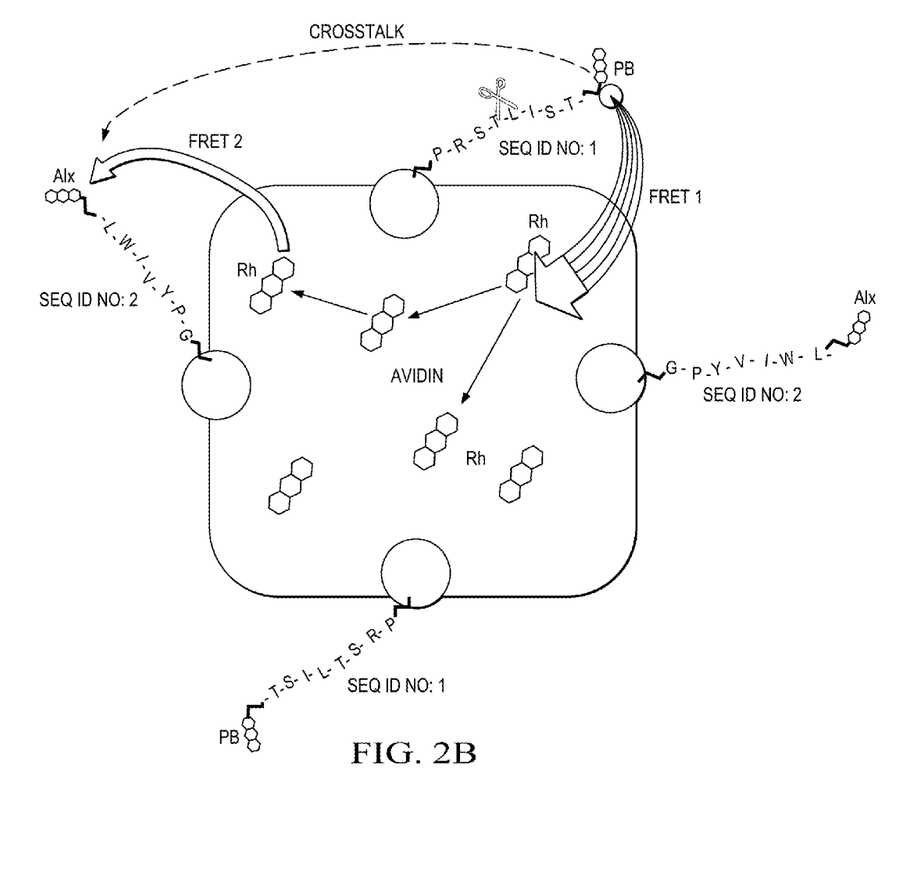
FIG. 2B shows an alternative multiplex probe based on two-step FRET process using avidin.

One example of a spacer for use with the present invention is shown schematically in FIGS. 2A and 2B, in which four binding sides for biotin may hold up to 4 or more peptides, and the significant size of avidin acts as a spacer, preventing the collapse of peptides onto neighbor peptides without the need for a rigid linker. In FIGS. 2A and 2B, the following exemplary amino acid sequences are depicted, however, the skilled artisan will recognize that the linker could be nucleic acids, carbohydrates, lipids, or other organic or inorganic modules that can be cleaved either specifically or non-specifically in situ. The following sequences are shown in FIGS. 2A and 2B: Pro-Arg-Ser/Thr-Leu/Ile-SER/Thr (SEQ ID NO.1) or Gly-Pro-Tyr-Val-Ile-Trp-Leu (SEQ ID NO.: 2). The spacer length will generally be selected to optimize the signal-to-noise ratio for the interaction of the two specific fluorophores and/or quenchers selected.

Matrix metalloproteinases (MMPs) are involved in major human diseases such as cancer, AIDS, and inflammation [1-3]. Therefore, sensitive detection and imaging of MMPs activities offer great clinical value to cancer detection, treatment, and therapy monitoring. Among many successful approaches that utilize peptide chemistry Förster resonance energy transfer (FRET) offers high potential for development of in-vitro and in-vivo proteases assays [4-8]. Recently we developed and tested a specific peptide sequence that is a substrate for MMP-9 (Lys-Gly-Pro-Arg-Ser-Leu-Ser-Gly-Lys) (SEQ ID NO.: 3) (FIG. 4), which is cleaved into Lys-Gly-Pro-Arg-Ser (SEQ ID NO.: 4) and Leu-Ser-Gly-Lys (SEQ ID NO.: 5). Other non-limiting sequence targets can include, e.g., peptide substrates for a consensus for MMP-2 (Lys-Gly-Ser-Gly-Pro-Tyr-Val-Ile-Trp-Leu-Gly-Lys) (SEQ ID NO.: 6) (SEQ ID NO.: 7). In this approach, one end of the specific peptide was labeled with a donor and the other with an acceptor chromophore. A selective cleavage of this specific peptide sequence by MMP-9 protease results in the separation of the two segments of oligopeptide carrying the donor and acceptor and consequently leads to significant increase of donor signal and decrease in acceptor signal. A ratiometric approach allows excellent dynamic range for detection that produces an almost 60 fold change when going from intact to completely cleaved peptide [7, 8].

The excellent sensitivity of such design offers a great opportunity to develop a pallet of assays for detecting the activities of various proteases and opens possibilities for many diagnostics applications. Detecting a single protease (like in our MMP-9 assay) is a promising step in disease/cancer detection, but usually it is not sufficient for adequate diagnosis. Typically the composition of multiple proteases and their relative ratio constitutes a much more powerful diagnostic indicator. A singleplex assay quantifies one analyte per assay and consequently n target proteases would require n independent assays. But multiplex assays offer the possibility for obtaining more reliable quantitative information on two or more analytes in a highly parallel analysis [9, 10].

For practical diagnostics applications in cellular and tissue imaging of proteases activities, the use of n independent substrates for detecting n proteases presents one more fundamental problem for quantitative detection: accessibility of the place of interest (like a cell or cancerous tissue) can be different for various probes, and relative evaluation of actual concentrations of individual proteases could be difficult or even be miss-leading. Therefore constructing a single probe that can simultaneously detect two or more proteases is of principle interest for cellular and tissue imaging applications.

The present invention can be used for a wide variety of detection purposes. One example of the detection is the development and use of the multiplex probes in cellular and tissue imaging. The present invention will dramatically speed-up and increase precision of enzyme activities detection. Also, these probes will be beneficial for high throughput assay applications substituting typical multiplex assays constructed from individual sensors.

EXAMPLE 1

A large family of Matrix Metalloproteinases (MMP-9, MMP-2, MMP-7, MMP-3, and more) are zinc-dependent endopeptidases. Many of them like MMP-9 and MMP-2 are widespread in human malignancies, and are known to facilitate tumor expansion and promote metastasis by mediating the degradation of basement-membrane and connective-tissue barriers. For example MMP-9 digests type IV collagen, laminin, and fibronectin; the major components of the basal lamina around blood vessels. MMP-9 is also known to be involved in the splitting of cell-surface receptors, the activation or inactivation of different cytokines and/or chemokines, and the release of apoptotic ligands. In addition MMP-9 plays an important role in cell proliferation, migration, differentiation, angiogenesis, as well as apoptosis. Overexpression of MMPs in tumor tissue and stroma can result in increased levels of activity of these enzymes in various body fluids such as blood or urine. It is a general understanding that increased expression of various MMPs correlates with more severe prognoses in cancer patients [2-10]. Therefore, measuring proteases activity constitutes attractive diagnostic tool. Such diagnostic tool becomes especially powerful when relative activities of different proteases can be simultaneously assessed. This has been achieved in in-vitro in multiplex format assays where two and more proteases are measured simultaneously in parallel manner. Such multiplex approach utilizes two or more sensors incorporated in one physical platform. A big advantage of multiplex analyses is the higher confidence in comparisons made between different samples, such as the comparison of two closely related proteases for example MMP-2 and MMP-9. This approach has been proved superior and much more precise than just simple sum of individual components.

Unfortunately such approach is much more difficult to be realized in-vivo in cellular or tissue environment. For example different accessibility to cell or specific tissue of various individual probes (sensors) may severely impact results leading to test misinterpretation. Up to now we are not alert of existence of peptide based fluorescence probe capable of simultaneous detection (relative activity assessment) of two or more proteases simultaneously in the same place in the cell or tissue by the single probe.

Figure 1:
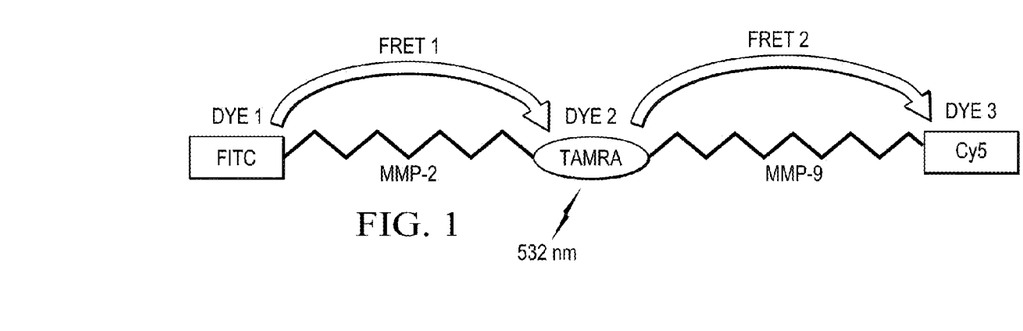
FIG. 1 is an embodiment that shows the single multiplex probe for detecting the MMP-2 and MMP-9 activities. Already a single wavelength excitation of the first dye may yield information on relative proteases activities. Unequivocally two wavelength interleave excitation allows to monitor two step FRET pathway and independently detect cleavage of peptide MMP-2 and MMP-9.

At the present, fluorescence based probe cannot consistently be used to simultaneously detect more than one protease in cells due to variations in probe uptake. The present invention is a true multiplex probe that can simultaneously detect the activity of two proteases. The overall design is presented in FIG. 1 in which single multiplex probe for the detecting of the activity of MMP-2 and MMP-9. Two wavelength interleave excitation allows to monitor two step Förster Resonance Energy Transfer (FRET) pathway and detect cleavage of peptide MMP-2 and MMP-9. Two oligopeptides, one specific for MMP-9 and the second to MMP-2 are attached to a central body. The free end of peptide 1 is labeled with a single fluorophore (Dye 1) that has short wavelength absorption (e.g. FITC). The free end of the second peptide is labeled with a single fluorophore (Dye 3) with long wavelength absorption (e.g. Cy5). The middle part, connecting two peptides is labeled with Dye 2 of intermediate absorption (e.g. TAMRA). The common expectation is that after excitation of the short wavelength fluorophore (Dye 1) with 480 nm, the energy transfer pathway will lead exclusively and with high efficiency (>90%) to the central part. From the central part, the excitation energy is transferred to the long wavelength absorbing fluorophore (Cy5). The relative fluorescence signal observed from the short, intermediate, and long wavelength fluorophores (FITC, TAMRA, and Cy5) will change as some of the oligopeptides are cleaved, and the change will be specific to which oligopeptide has been cleaved (MMP-2, or MMP-9, or both). The specificity is achieved by a dual excitation scheme: 480 nm for FITC and 532 nm for TAMRA.

The present inventors can design, develop, build, and test a fluorescent probe based on the avidin/biotin-oligopeptides construct. The labeling of avidin can be optimized with multiple dyes (e.g. TAMRA). Binding of labeled oligopeptides to avidin through biotin binding can also be optimized.

The present inventors can also develop probe specificity of response to various proteases and test the response to MMP-2, MMP-9, and a mixture of both, and test if the response is specific and independent from other proteases (e.g. MMP-7, MMP-10, etc.).

The present inventors have demonstrated that MMP-9 very effectively cleaves a peptide (Lys-Gly-Pro-Arg-Ser-Leu-Ser-Gly-Lys) [7, 8]. They have also shown that the peptide is very specific and is not digested by MMP-2 enzyme MMP-3 or MMP-7 enzymes [7, 8]. FRET sensitized fluorescence detection proves to be very effective detection approach. Similar specific peptide sequences have been developed for MMP-2, MMP-7 and more. To make highly confident assessment of various proteases activities directly in cells and tissue it is necessary to have single molecular probe capable for simultaneous analysis/detection of more than one protease. The present invention includes methods for developing and constructing a new probe that will be capable of simultaneous detection of activities of two proteases (like MMP-2 and MMP-9) at the same time and the same place by the same molecule (molecular construct). This approach uses Förster resonance energy transfer (FRET) that can be highly enhanced when multiple acceptors are used [11]. The probe is constructed in a way to force two sequential steps of energy transfer process. First step (FRET 1), is mediated through the cleavable linker specific to enzyme 1 (for example MMP-9) and occurs between the first energy donor and first acceptor (acceptor is a central body). Second step (FRET 2), is between the first acceptor that becomes donor to the second acceptor. The second donor and second acceptor are separated by linker specific to enzyme 2 (for example MMP-2). A highly efficient well-defined sequential FRET process offers distinctive signatures for recognizing two proteins activities. Use of pulse interleaved excitation (independent excitations of the first donor and first acceptor/second donor) opens detection scheme that eliminates ubiquities typically associated with single wavelength excitation and multiple steps FRET process.

The present invention overcomes a critical problem with pairs of fluorescence based probes could simultaneously be used for detecting more than one protease. The problem is that FRET pairs can enter cells differentially, that is, it is not possible guarantee that both separate probes are absorbed, bound to, or endo- or pinocytosed into the target cells. This embodiment is presented in FIG. 2A in which two oligopeptides, one specific for MMP-9 and second to MMP-2 are attached to a central (protein) body. The free end of peptide 1 is labeled with single fluorophore that has short wavelength absorption (e.g. FITC). The free end of second peptide is labeled with single fluorophore with long wavelength absorption (e.g., Cy5). The middle part, protein core, is labeled with few dyes of intermediate absorption (e.g., Texas Red, TR).

The multiple labeling of central body ensure that after excitation of the short wavelength fluorophore (Donor 1) with 480 nm the energy transfer pathway will exclusively lead with very high efficiency (>90%) to the central part. From the central part the excitation energy is transferred to the long wavelength absorbing fluorophore (Cy5) with lower efficiency (<90%). The relative fluorescence signal observed for FITC, TR, and Cy5 will change as some of the oligopeptides are cleaved and the change will be specific to which oligopeptide has been cleaved (MMP-2, or MMP-9, or both). The specificity can be increased by using dual excitation scheme 480 nm for FITC and 532 nm for TR, such an excitations can be used in so call interlive mode (one excitation and one detection at the same time). FIG. 2B shows an alternative multiplex probe based on two-step FRET process using Avidin.

Peptide based detection. Matrix metalloproteinases (MMPs) are a family of a large number of different zinc-dependent endopeptidases, which are mainly responsible for the degradation of extracellular matrix (ECM) proteins such as collagens, fibronectin, proteoglycans, and elastin. Proteases play an important role in development, tissue remodelling, wound healing and inflammation [12, 13] and have been involved in major human diseases such as cancer, AIDS, inflammation, and neurodegenerative disease [1-3]. The level and activities of various MMPs are frequently found to correlate with advanced tumor stage, increased invasion and metastasis [14-18]. Therefore, sensitive detection and imaging of MMPs activities offers a great clinical value to cancer detection and therapy monitoring.

Development of methods to assay proteases and their inhibition that will have high sensitivity and high specificity is a focus of many research efforts. Such methods especially with capability for multiplexed detection are of great significance in diagnosis of protease-relevant diseases and are essential for development of potential drugs and treatment [1-3, 19]. In recent years, a number of approaches have been developed based on gel electrophoresis and/or liquid chromatography to assay proteases [9, 10], but most of these highly sensitive methods have significant limitation when applied in high-throughput/multiplex assay format. Recently fluorescence-based detection [12, 13] brought much attention and many successful approaches utilizing peptide chemistry and Forester resonance energy transfer (FRET) have been developed for in-vitro and in-vivo proteases assays [5-8].

Figure 3A:
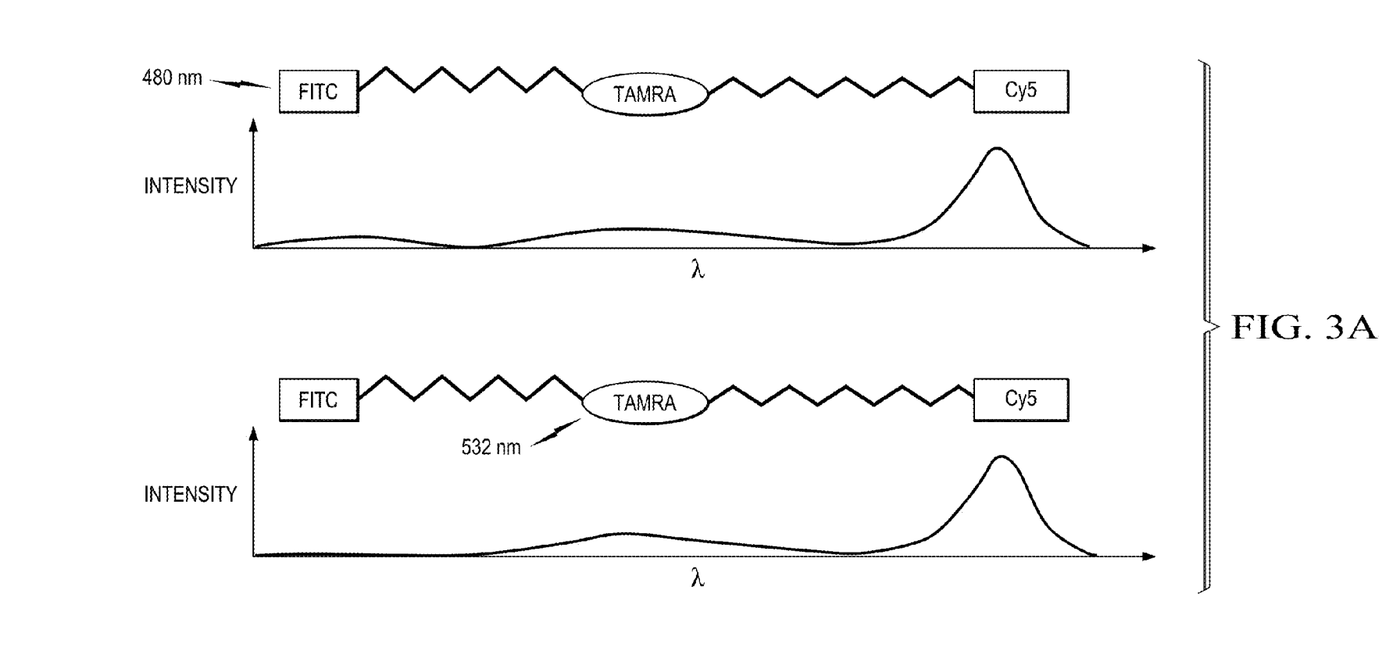
FIG. 3A—intact probe.
Figure 3B:
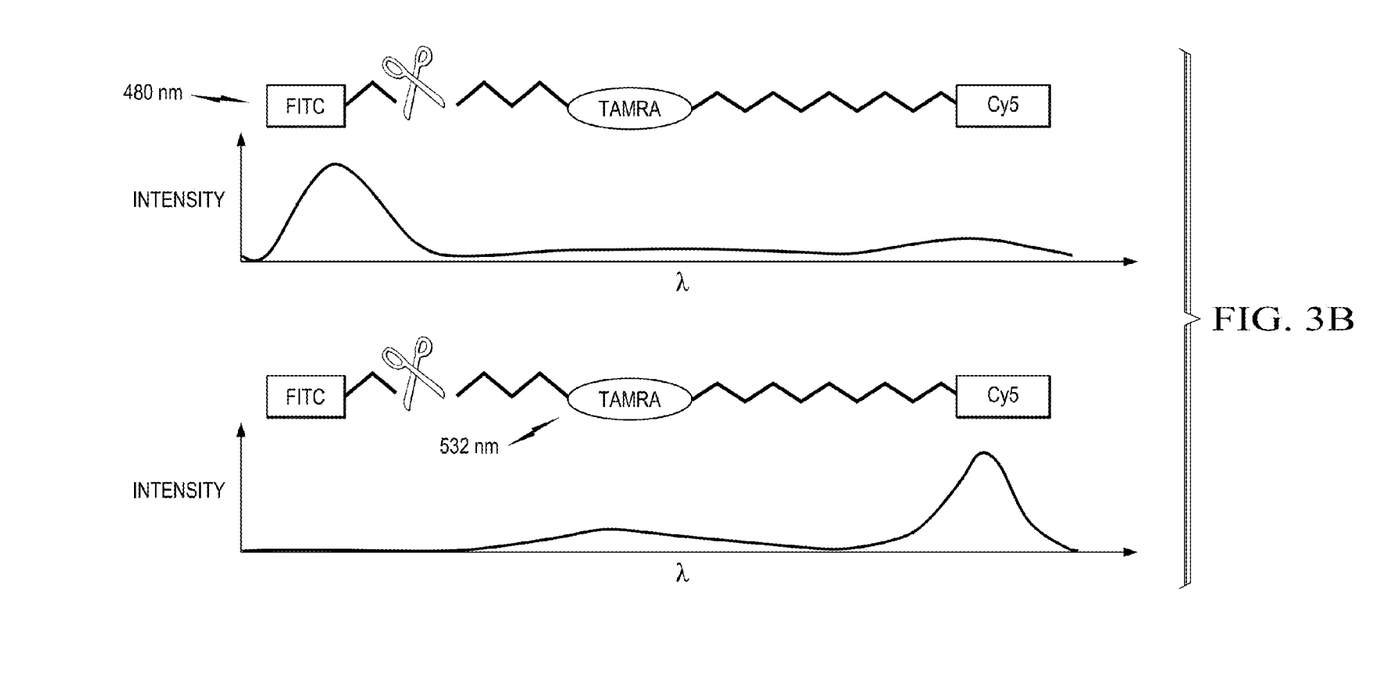
FIG. 3B—MMP-2 peptide cleaved.
Figure 3C:
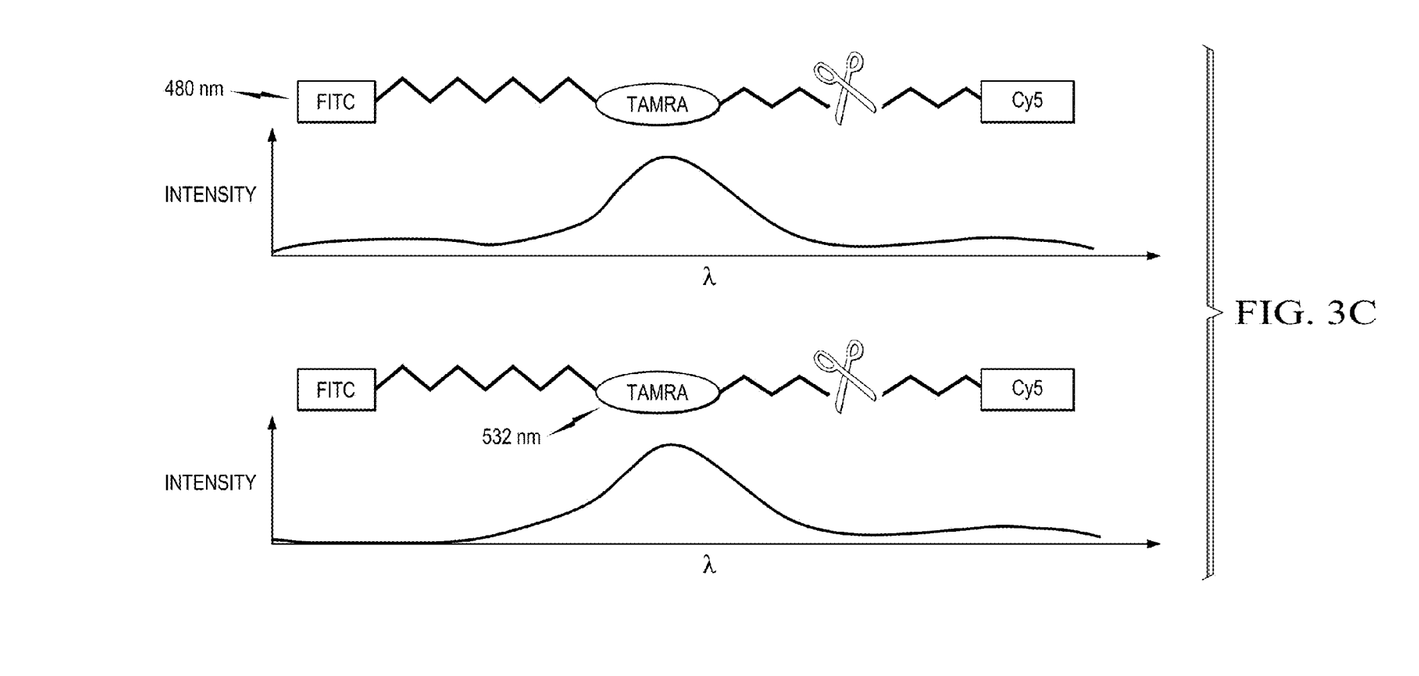
FIG. 3C—MMP-9 peptide cleaved.
Figure 3D:
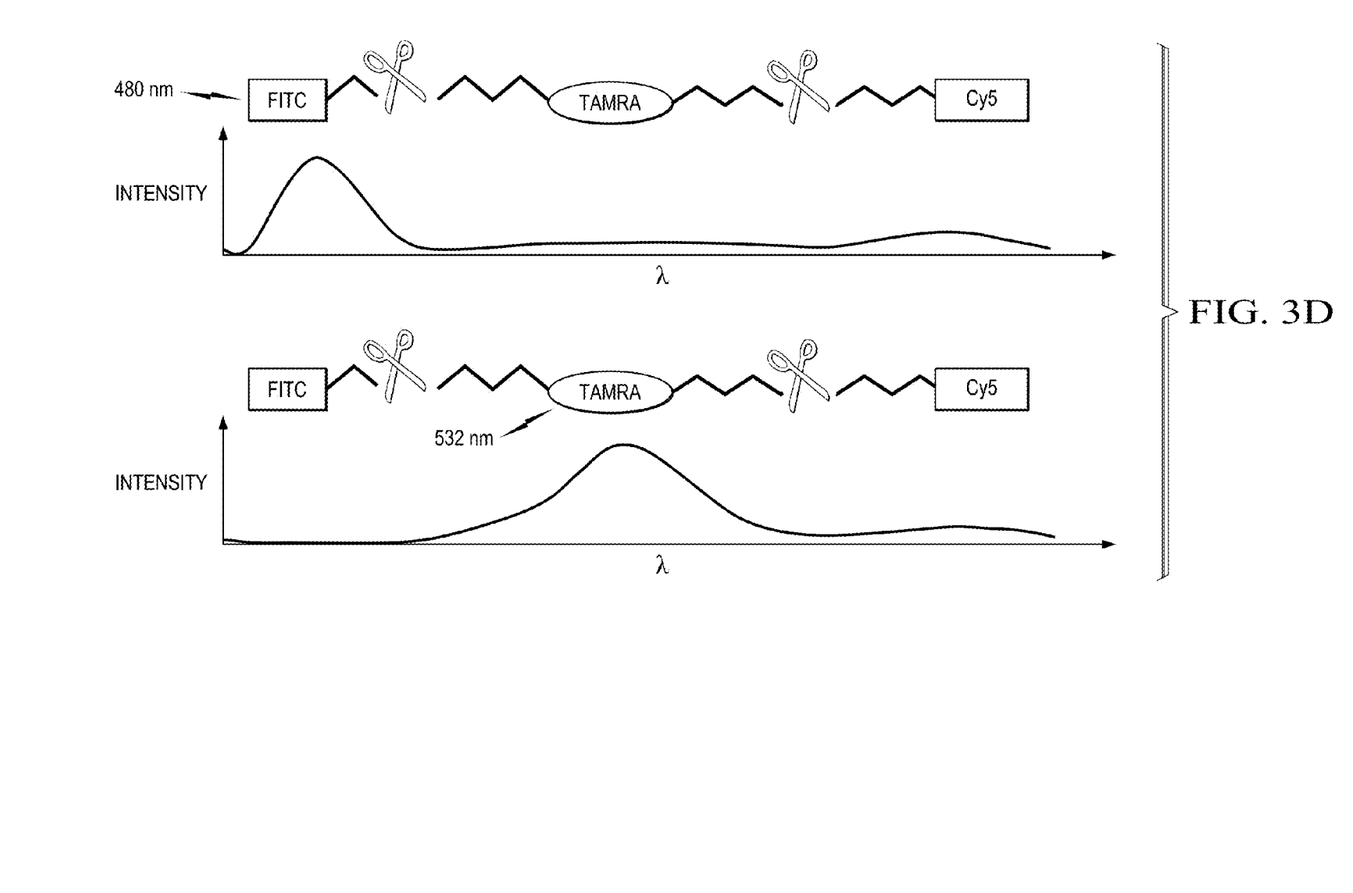

How the detection scheme works. FIGS. 3A to 3D show schematic representations of how sequential FRET sensor will work. The principle assumption is that only (preferentially) sequential FRET 1 and FRET 2 occurs and the direct transfer from FITC to Cy5 is negligible. The probe is built in such way that both pathways (FRET 1 and FRET 2) will have high efficiency (~90%) and direct transfer from FITC to Cy5 will be very low (below 10%). It is interesting to note that for each excitation we have four distinct possibilities. The example in FIG. 3A shows the signal from the intact probe. In FIG. 3B, for both excitations, a dominant long wavelength emission from Dye 3 (Cy5) is shown in red. The peptide MMP-2 is cleaved (FRET 1 broken). Excitation 480 nm will show blue fluorescence of Dye 1 (FITC in our case) since there will not be FRET. For excitation 532 nm the response will be similar to (A)—red emission of Cy5. In FIG. 3C the signal is shown when the peptide MMP-9 is cleaved (FRET 2 broken). For 480 nm excitation we will only see Dye 2 (orange emission) since only FRET 1 will occur. For 532 nm excitation we will only see also Dye 2 (orange emission). In FIG. 3D both peptides are cleaved (no FRET 1 or FRET 2).

For 480 nm excitation we will see only blue fluorescence of Dye 1 and for 532 nm orange fluorescence of Dye 2.

At 480 nm for both steps (3B) and (3D) the signals are undistinguishable (give the same response) and for 532 nm excitation steps (3C) and (3D) gives the same response. However, a combination of both readings will always give unique answer.

Figure 4:
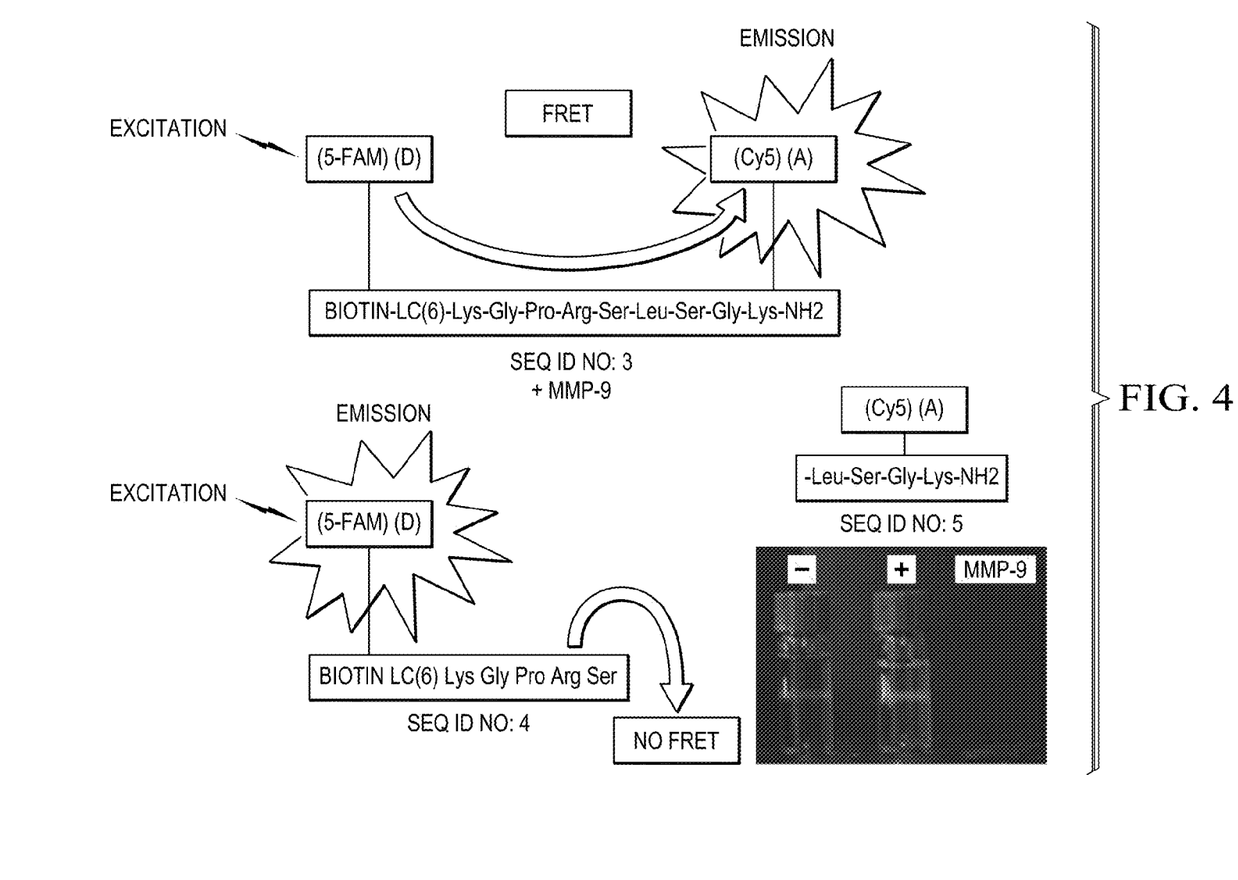
FIG. 4 is an example of the FRET based probe for detecting MMP-9 activity. Specific oligopeptide sequence (for example, SEQ ID NO.: 3, which is cleaved into SEQ ID NO.

FIG. 4 shows a FRET based probe for detecting MMP-9 activity. A specific oligopeptide sequence was labeled with donor on one end and acceptor on another end. When intact, significant (>90%) FRET occurs. Addition of MMP-9 cleaves the peptide separating donor and acceptor. Photography shows the color change induced by cleavage.

An enhanced FRET to multiple acceptors allows forcing a first step (FRET 1) dominantly to the first acceptor. Many of prior trials failed since second acceptor is typically also good acceptor to first donor and significant FRET occurs from donor 1 directly to acceptor 2 (bypassing the acceptor 1—FRET 1). Also a large macromolecular body function as a convenient special constrains preventing close approach of donor 1 by acceptor 2.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof"

is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Overall, C. M.; Kleifeld, O. Validating matrix metalloproteinases as drug targets and anti-targets for cancer therapy. Nat. Rev. Cancer 2006, 6, 227-239.
2. Concha, N. O.; Abdel-Meguid, S. S. Controlling Apoptosis by Inhibition of Caspases. Curr. Med. Chem. 2002, 9, 713-726.
3. Schwienhorst, A. Direct thrombin inhibitors—a survey of recent developments. Cell. Mol. Life Sci. 2006, 63, 2773-2791.
4. Shi, L.; De Paoli, V.; Rosenzweig, N.; Rosenzweig, Z. Synthesis and Application of Quantum Dots FRET-Based Protease Sensors. J. Am. Chem. Soc. 2006, 128, 10378-10379.
5. Medintz, I. L.; Clapp, A. R.; Brunel, F. M.; Tiefenbrunn, T.; Uyeda, H. T.; Chang, E. L.; Deschamps, J. R.; Dawson, P. E.; Mattoussi, H. Proteolytic activity monitored by fluorescence resonance energy transfer through quantum-dot-peptide conjugates. Nat. Mater. 2006, 5, 581-589.
6. Chang, E.; Miller, J. S.; Sun, J.; Yu, W. W.; Colvin, V. L.; Drezek, R.; West, J. L. Protease-activated quantum dot probes. Biochem. Biophys. Res. Commun. 2005, 334, 1317-1321.
7. Fudala R, Ranjan A P, Mukerjee A, Vishwanatha J K, Gryczynski Z, Borejdo J, Sarkar P, Gryczynski I. Fluorescence detection of MMP-9. I—MMP-9 selectively cleaves Lys-Gly-Arg-Ser-Leu-Ser-Gly-Lys peptide. Current Pharmaceutical Biotechnology. 2011 May 1; 12(5):834-838.
8. Fudala R, Rich R, Mukerjee A, Ranjan A P, Vishwanatha J K, Kurdowska A K, Gryczynski Z, Borejdo J, Gryczynski I. Fluorescence Detection of MMP-9. II. Ratiometric FRET-Based Sensing With Dually Labeled Specific Peptide. Current Pharmaceutical Biotechnology. 2012 Feb. 20. [Epub ahead of print].
9. Bjurlin, M. A.; Bloomer, S.; Nelson, C. J. Characterization of proteolytic activity of proteases. Biotechnol. Lett. 2002, 24, 191-195.
10. Zhao, Z.; Raftery, M. J.; Niu, X. M.; Daja, M. M.; Russell, P. J. Application of in-gel protease assay in a biological sample: characterization and identification of urokinase-type plasminogen activator (uPA) in secreted proteins from a prostate cancer cell line PC-3. Electrophoresis 2004, 25, 1142-1148.
11. Maliwal B P, Raut S, Fudala R, D'Auria S, Marzullo V M, Luini A, Gryczynski I, Gryczynski Z. Extending FRET Measurements Beyond 100 Å; with Commonly Used Organic Fluorophores: Enhanced Transfer in the Presence of Multiple Acceptors. Journal of Biomedical Optics; (2012); 17(1), 011006, doi:10.1117/1.JBO.17.1.011006.
12. Werb Z. ECM and cell surface proteolysis: regulating cellular ecology. Cell 1997; 91:439-42. [PubMed: 9390552].
13. Mott J D, Werb Z. Regulation of matrix biology by matrix metalloproteinases. Curr Opin Cell Biol. 2004; 16:558-64. [PubMed: 15363807].
14. Fingleton B. Matrix metalloproteinases: Roles in cancer and metastasis. Front Biosci. 2006; 11:479-491. [PubMed: 16146745].
15. Egeblad M, Werb Z. New functions for the matrix metalloproteinases in cancer progression. Nat Rev Cancer 2002; 2:161-174. [PubMed: 11990853].
16. Brinckerhoff C E, Matrisian L M. Matrix metalloproteinases: a tail of a frog that became a prince. Nat Rev Mol Cell Biol 2002; 3:207-214. [PubMed: 11994741].
17. Bachmeier B E, Iancu C M, Jochum M, Nerlich A G. Matrix metalloproteinases in cancer: comparison of known and novel aspects of their inhibition as a therapeutic approach. Expert Rev Anticancer Ther 2005; 5:149-163.
18. Overall C M, Kleifeld O. Tumour microenvironment—opinion: validating matrix metalloproteinases as drug targets and anti-targets for cancer therapy Nature Rev Cancer 2006; 6:227-239. [PubMed: 16498445].
19. White, C. M. Thrombin-directed inhibitors: pharmacology and clinical use. Am. Heart J. 2005, 149, 54-60.

What is claimed is:

1. A fluorescence-based multiplex probe to simultaneously detect two or more proteinase activities comprising:
    at least one first oligopeptide having a first end of the first oligopeptide and a second end of the first oligopeptide, wherein the first end of the first oligopeptide is attached to a central body and the second end of the first oligopeptide is attached to a first fluorophore;
    at least one second oligopeptide having a first end of the second oligopeptide and a second end of the second oligopeptide, wherein the first end of the second oligopeptide is attached to the central body and the second end of the second oligopeptide is attached to a third fluorophore;
    wherein the central body comprises at least one second fluorophore; wherein the first oligopeptide comprises a specific cleavage site of a first proteinase; and
    wherein the second oligopeptide comprises a specific cleavage site of a second proteinase.

2. The multiplex probe of claim 1, wherein the first fluorophore has a shorter wavelength absorption then the second fluorophore, and the second fluorophore has a shorter wavelength absorption then the third fluorophore.

3. The multiplex probe of claim 2, wherein a fluorescent emission peak of the first fluorophore overlaps with an excitation peak of the second fluorophore, and wherein a fluorescent emission peak of the second fluorophore overlaps with an excitation peak of the third fluorophore.

4. The multiplex probe of claim 1, wherein the first fluorophore is defined as donor chromophore for the second fluorophore; wherein the second fluorophore is defined as acceptor chromophore of the first fluorophore and further defined as donor chromophore for the third fluorophore; and wherein the third fluorophore is defined as acceptor chromophore for the second fluorophore.

5. The multiplex probe of claim 1, wherein the first fluorophore comprises FITC, the second fluorophore comprises TAMRA, and the third fluorophore comprises Cy5.

6. The multiplex probe of claim 1, wherein the direct energy transfer from the first fluorophore to the second fluorophore is disabled by an enzyme.

7. The multiplex probe of claim 1, wherein the first or second proteinase is a matrix metalloproteinase.

8. The multiplex probe of claim 1, wherein the central body is a nanoparticle.

9. The multiplex probe of claim 1, wherein the central body comprises a spacer that limits direct contact of the first and the second oligopeptide.

10. The multiplex probe of claim 1, wherein the central body comprises avidin.

11. The multiplex probe of claim 1, wherein the first or the second oligopeptide comprises a specific cleavage site for: MMP-9 or MMP-2.

12. The multiplex probe of claim 1, wherein the first or the second oligopeptide comprises at least one specific cleavage site selected from the group consisting of optimal peptide substrates for a consensus for MMP-2 (Lys-Gly-Ser-Gly-Pro-Tyr-Val-Ile-Trp-Leu-Gly-Lys) (SEQ ID NO.: 6).

13. The multiplex probe of claim 1, wherein the first or the second oligopeptide comprises at least one sequence selected from the group consisting of optimal substrate (peptide sequence) consensus for MMP-9 (Lys-Gly-Pro-Arg-Ser/Thr-Leu/Ile-Ser/Thr-Gly-Lys) (SEQ ID NO.: 7).

14. A method of simultaneously detecting proteinase activity of at least two proteinases in a sample comprising:
    obtaining the sample;
    obtaining a fluorescence-based multiplex probe, the probe comprising at least one first oligopeptide having a first end of the first oligopeptide and a second end of the first wherein the first end of the first oligopeptide is attached to a central body and the second end of the first oligopeptide is attached to a first fluorophore;
    at least one second oligopeptide having a first end of the second oligopeptide and a second end of the second oligopeptide, wherein the first end of the second oligopeptide is attached to the central body and the second end of the second oligopeptide is attached to a second fluorophore; wherein the central body comprises at least one third fluorophore;
    wherein the first oligopeptide comprises a specific cleavage site of a first proteinase, wherein the second oligopeptide comprises a specific cleavage site of a second proteinase;
    combining the sample with the fluorescence-based multiplex probe;
    exposing the sample to a first excitation wavelength for the first fluorophore and detecting a FRET emission, wherein the FRET emission comprises a first emission of the first fluorophore, a second emission of the second fluorophore, and a third emission of the third fluorophore;
    relating the first emission to the second emission;
    relating the first emission to the third emission; and
    determining proteinase activity.

15. A method of diagnosing a patient suspected of being afflicted with a disease comprising:
    obtaining a sample of the patient; obtaining a fluorescence-based multiplex probe, the probe comprising at least one first oligopeptide having a first end of the first oligopeptide and a second end of the first oligopeptide, wherein the first end of the first oligopeptide is attached to a central body and the second end of the first oligopeptide is attached to a first fluorophore;
    at least one second oligopeptide having a first end of the second oligopeptide and a second end of the second oligopeptide, wherein the first end of the second oligopeptide is attached to the central body and the second end of the second oligopeptide is attached to a second fluorophore;
    wherein the central body comprises at least one third fluorophore;
    wherein the first oligopeptide comprises a specific cleavage site of a first proteinase, wherein the second oligopeptide comprises a specific cleavage site of a second proteinase;

combining the sample with the fluorescence-based multiplex probe;

exposing the sample to a first excitation wavelength for the first fluorophore and detecting a FRET emission, wherein the FRET emission comprises a first emission of the first fluorophore, a second emission of the second fluorophore, and a third emission of the third fluorophore;

relating the first emission to the second emission;

relating the first emission to the third emission;

determining proteinase activity; and diagnosing cancer upon relating proteinase activity to diagnosis of the disease.

16. The method of claim 15, wherein the sample is a tumor sample or a tumor sample from a body fluid.

17. The method of claim 15, wherein diagnosing comprises predicting a therapeutic outcome of an anti-cancer treatment or changing the treatment depending on the presence or absence of markers determined to determine the pharmacokinetics of a treatment for the disease.

18. The method of claim 15, wherein the disease is cancer.

* * * * *

SEQUENCE LISTING

<160> NUMBER OF SEQ ID NOS: 7

<210> SEQ ID NO 1
<211> LENGTH: 8
<212> TYPE: PRT
<213> ORGANISM: Artificial Sequence

```
<220> FEATURE:
<223> OTHER INFORMATION: Synthetic peptide

<400> SEQUENCE: 1

Pro Arg Ser Thr Leu Ile Ser Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Gly Pro Tyr Val Ile Trp Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Lys Gly Pro Arg Ser Leu Ser Gly Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Lys Gly Pro Arg Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Leu Ser Gly Lys
1

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Lys Gly Ser Gly Pro Tyr Val Ile Trp Leu Gly Lys
1               5                   10

<210> SEQ ID NO 7
<211> LENGTH: 12
<212> TYPE: PRT
<213> ORGANISM: Artificial Sequence
<220> FEATURE:
```

-continued

<223> OTHER INFORMATION: Synthetic peptide

<400> SEQUENCE: 7

Lys Gly Pro Arg Ser Thr Leu Ile Ser Thr Gly Lys
1               5                   10